United States Patent [19]

Kalsheker

[11] Patent Number: 5,412,073
[45] Date of Patent: May 2, 1995

[54] POLYPEPTIDES AND DNA CODING THEREFOR

[75] Inventor: Ahmed N. Kalsheker, Cardiff, Wales

[73] Assignee: 3i Research Exploitation Limited, London, England

[21] Appl. No.: 859,480

[22] PCT Filed: Dec. 21, 1990

[86] PCT No.: PCT/GB90/02003
§ 371 Date: Jun. 16, 1992
§ 102(e) Date: Jun. 16, 1992

[87] PCT Pub. No.: WO91/09947
PCT Pub. Date: Jul. 11, 1991

[30] Foreign Application Priority Data

Dec. 22, 1989 [GB] United Kingdom ............... 8929110

[51] Int. Cl.⁶ ..................... C07K 13/00; A61K 37/64
[52] U.S. Cl. ..................................... 530/350; 530/395
[58] Field of Search ............... 530/350, 395, 333, 846, 530/830; 514/2, 8

[56] References Cited

FOREIGN PATENT DOCUMENTS 0164719 12/1985 European Pat. Off. .
0222726  5/1987 European Pat. Off. .

OTHER PUBLICATIONS

Clarke–Lewis et al 1986. Science 231:134–139.
Long et al. 1984 Biochemistry 23:4828–4837.
Chem. Abstracts 100 (1984) :405 #155002j.

Primary Examiner—Charles L. Patterson, Jr.
Attorney, Agent, or Firm—Edward S. Irons

[57] ABSTRACT

A serine protease inhibitor, similar in some respects to $\alpha_1$-antitrypsin (AAT) but having an unglycosylated molecular weight on PAGE of $32\pm1$ kDa, has been discovered. cDNA encoding the active protein has been cloned and sequenced, so the sequence of the protein has been revealed. Recombinant DNA technology enables the natural polypeptide sequence and related proteins to be prepared, for example by expression in *E. coli*. The inhibitor may prove useful in the treatment of emphysema, arthritis or septic shock.

2 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 1339
( B ) TYPE: Nucleic Acid
( C ) STRANDEDNESS: Double
( D ) TOPOLOGY: Linear ( i i ) MOLECULE TYPE: DNA (genomic)

( i x ) FEATURE:
( A ) NAME/KEY: CDS
( B ) LOCATION: 3..926

( x i ) SEQUENCE DESCRIPTION: SEQ ID NO: 1:

```
GG ATC CTC AGC CAG GGA GAC AGG GAC CAG GCA GCA CAG              38
   Ile Leu Ser Gln Gly Asp Arg Asp Gln Ala Ala Gln
   1             5                   10

GCC TGC CAG CAG GAG GAT GCC CCA CGA GAC AGA AGA                 74
Ala Cys Gln Gln Glu Asp Ala Pro Arg Asp Arg Arg
        15                  20

CGG CAT TGT CGA TTC ACT GTC CCA GGT CAG TGG TGG                 110
Arg His Cys Arg Phe Thr Val Pro Gly Gln Trp Trp
25                  30                      35

TGC CTG AAG CTA GTG GAT AAG TTT TTG GAG GAT GTT                 146
Cys Leu Lys Leu Val Asp Lys Phe Leu Glu Asp Val
            40                  45

AAA AAG TTG TAC CAC TCA GAA GCC TTC ACT GTC AAC                 182
Lys Lys Leu Tyr His Ser Glu Ala Phe Thr Val Asn
        50                  55                  60

TTC GGG GAC ACC GAA GAG GCC AAG AAA CAG ATC AAC                 218
Phe Gly Asp Thr Glu Glu Ala Lys Lys Gln Ile Asn
                65                  70

GAT TAC GTG GAG AAG GGT ACT CAA GGG AAA ATT GTG                 254
Asp Tyr Val Glu Lys Gly Thr Gln Gly Lys Ile Val
            75                  80

GAT TTG GTC AAG GAG CTT GAC AGA GAC ACA GTT TTT                 290
Asp Leu Val Lys Glu Leu Asp Arg Asp Thr Val Phe
85                  90                      95

GCT CTG GTG AAT TAC ATC TTC TTT AAA GGC AAA TGG                 326
Ala Leu Val Asn Tyr Ile Phe Phe Lys Gly Lys Trp
            100                 105

GAG AGA CCC TTT GAA GTC AAG GAC ACC GAG GAA GAG                 362
Glu Arg Pro Phe Glu Val Lys Asp Thr Glu Glu Glu
    110                 115                 120

GAC TTC CAC GTG GAC CAG GTG ACC ACC GTG AAG GTG                 398
Asp Phe His Val Asp Gln Val Thr Thr Val Lys Val
                125                 130

CCT ATG ATG AAG CGT TTA GGC ATG TTT AAC ATC CAG                 434
Pro Met Met Lys Arg Leu Gly Met Phe Asn Ile Gln
        135                 140

CAC TGT AAG AAG CTG TCC AGC TGG GTG CTG CTG ATG                 470
His Cys Lys Lys Leu Ser Ser Trp Val Leu Leu Met
145                 150                 155

AAA TAC CTG GGC AAT GCC ACC GCC ATC TTC TTC CTG                 506
Lys Tyr Leu Gly Asn Ala Thr Ala Ile Phe Phe Leu
            160                 165

CCT GAT GAG GGG AAA CTA CAG CAC CTG GAA AAT GAA                 542
```

```
          Pro  Asp  Glu  Gly  Lys  Leu  Gln  His  Leu  Glu  Asn  Glu
               170                 175                      180

CTC  ACC  CAC  GAT  ATC  ATC  ACC  AAG  TTC  CTG  GAA  AAT                   578
Leu  Thr  His  Asp  Ile  Ile  Thr  Lys  Phe  Leu  Glu  Asn
               185                           190

GAA  GAC  AGA  AGG  TCT  GCC  AGC  TTA  CAT  TTA  CCC  AAA                   614
Glu  Asp  Arg  Arg  Ser  Ala  Ser  Leu  His  Leu  Pro  Lys
          195                           200

CTG  TCC  ATT  ACT  GGA  ACC  TAT  GAT  CTG  AAG  AGC  GTC                   650
Leu  Ser  Ile  Thr  Gly  Thr  Tyr  Asp  Leu  Lys  Ser  Val
205                      210                      215

CTG  GGT  CAA  CTG  GGC  ATC  ACT  AAG  GTC  TTC  AGC  AAT                   686
Leu  Gly  Gln  Leu  Gly  Ile  Thr  Lys  Val  Phe  Ser  Asn
               220                      225

GGG  GCT  GAC  CTC  TCC  GGG  GTC  ACA  GAG  GAG  GCA  CCC                   722
Gly  Ala  Asp  Leu  Ser  Gly  Val  Thr  Glu  Glu  Ala  Pro
     230                      235                      240

CTG  AAG  CTC  TCC  AAG  GCC  GTG  CAT  AAG  GCT  GTG  CTG                   758
Leu  Lys  Leu  Ser  Lys  Ala  Val  His  Lys  Ala  Val  Leu
               245                      250

ACC  ATC  GAC  GAG  AAA  GGG  ACT  GAA  GCT  GCT  GGG  GCC                   794
Thr  Ile  Asp  Glu  Lys  Gly  Thr  Glu  Ala  Ala  Gly  Ala
          255                           260

ATG  TTT  TTA  GAG  GCC  ATA  CCC  ATG  TCT  ATC  CCC  CCC                   830
Met  Phe  Leu  Glu  Ala  Ile  Pro  Met  Ser  Ile  Pro  Pro
265                      270                           275

GAG  GTC  AAG  TTC  AAC  AAA  CCC  TTT  GTC  TTC  TTA  ATG                   866
Glu  Val  Lys  Phe  Asn  Lys  Pro  Phe  Val  Phe  Leu  Met
               280                      285

ATT  GAA  CAA  AAT  ACC  AAG  TCT  CCC  CTC  TTC  ATG  GGA                   902
Ile  Glu  Gln  Asn  Thr  Lys  Ser  Pro  Leu  Phe  Met  Gly
     290                      295                      300

AAA  GTG  GTG  AAT  CCC  ACC  CAA  AAA                                       926
Lys  Val  Val  Asn  Pro  Thr  Gln  Lys
                    305

TAACTGCCTC  TCGCTCCTCA  ACCCCTCCCC  TCCATCCCTG                               966

GCCCCCTCCC  TGGATGACAT  TAAAGGATCC  GCAAGTTTCA                               1006

TGAGCTAAAA  TATTTAGCAC  TATCTACTTT  TTTTTTTTCT                               1046

TTTAAGGGT   TTTTTAAGAG  GGAGAAAAAA  ATGCACACAA                               1086

AGCAGTGAAT  AGTAGGCTAG  ACTCATTGGG  GGGTAATTAC                               1126

CCTAGACTCC  TAACTTTCCA  GGCTAGTTGA  GGAAACTAAG                               1166

GAATGCCTCC  CAATATTCCA  ACCCTCAAAG  CTCACACTGC                               1206

CCCCAGAAAA  ACAAAACACT  CACCCCCAAT  CCAATGAATC                               1246

ATCTGCATAG  AAAACCAGAG  CCAGCAGGCC  TAGGGAAGGA                               1286

GCGGATGTGT  GTTGCCCTCC  TCTACAACAT  ACCACTGAAC                               1326

TAGTATGTGC  TAG                                                              1339
```

( 2 ) INFORMATION FOR SEQ ID NO: 2:

( i ) SEQUENCE CHARACTERISTICS:
        ( A ) LENGTH: 308
        ( B ) TYPE: Amino Acid
        ( C ) STRANDEDNESS: Not Relevant
        ( D ) TOPOLOGY: Linear ( i i ) MOLECULE TYPE: Protein ( x i ) SEQUENCE DESCRIPTION: SEQ ID NO: 2:

-continued

| Ile 1 | Leu | Ser | Gln | Gly 5 | Asp | Arg | Asp | Gln | Ala 10 | Ala | Gln | Ala | Cys |
| Gln 15 | Gln | Glu | Asp | Ala | Pro 20 | Arg | Asp | Arg | Arg | His 25 | Cys | Arg | |
| Phe | Thr 30 | Val | Pro | Gly | Gln | Trp 35 | Trp | Cys | Leu | Lys | Leu 40 | Val | Asp |
| Lys | Phe | Leu 45 | Glu | Asp | Val | Lys | Lys 50 | Leu | Tyr | His | Ser | Glu 55 | Ala |
| Phe | Thr | Val | Asn 60 | Phe | Gly | Asp | Thr | Glu 65 | Glu | Ala | Lys | Lys | Gln 70 |
| Ile | Asn | Asp | Tyr | Val 75 | Glu | Lys | Gly | Thr | Gln 80 | Gly | Lys | Ile | Val |
| Asp 85 | Leu | Val | Lys | Glu | Leu 90 | Asp | Arg | Asp | Thr | Val 95 | Phe | Ala | Leu |
| Val | Asn 100 | Tyr | Ile | Phe | Phe | Lys 105 | Gly | Lys | Trp | Glu | Arg 110 | Pro | Phe |
| Glu | Val | Lys 115 | Asp | Thr | Glu | Glu | Glu 120 | Asp | Phe | His | Val | Asp 125 | Gln |
| Val | Thr | Thr | Val 130 | Lys | Val | Pro | Met | Met 135 | Lys | Arg | Leu | Gly | Met 140 |
| Phe | Asn | Ile | Gln | His 145 | Cys | Lys | Lys | Leu | Ser 150 | Ser | Trp | Val | Leu |
| Leu 155 | Met | Lys | Tyr | Leu | Gly 160 | Asn | Ala | Thr | Ala | Ile 165 | Phe | Phe | Leu |
| Pro | Asp 170 | Glu | Gly | Lys | Leu | Gln 175 | His | Leu | Glu | Asn | Glu 180 | Leu | Thr |
| His | Asp | Ile 185 | Ile | Thr | Lys | Phe | Leu 190 | Glu | Asn | Glu | Asp | Arg 195 | Arg |
| Ser | Ala | Ser | Leu 200 | His | Leu | Pro | Lys | Leu 205 | Ser | Ile | Thr | Gly | Thr 210 |
| Tyr | Asp | Leu | Lys | Ser 215 | Val | Leu | Gly | Gln | Leu 220 | Gly | Ile | Thr | Lys |
| Val 225 | Phe | Ser | Asn | Gly | Ala 230 | Asp | Leu | Ser | Gly | Val 235 | Thr | Glu | Glu |
| Ala | Pro 240 | Leu | Lys | Leu | Ser | Lys 245 | Ala | Val | His | Lys | Ala 250 | Val | Leu |
| Thr | Ile | Asp 255 | Glu | Lys | Gly | Thr | Glu 260 | Ala | Ala | Gly | Ala | Met 265 | Phe |
| Leu | Glu | Ala | Ile 270 | Pro | Met | Ser | Ile | Pro 275 | Pro | Glu | Val | Lys | Phe 280 |
| Asn | Lys | Pro | Phe | Val 285 | Phe | Leu | Met | Ile | Glu 290 | Gln | Asn | Thr | Lys |
| Ser 295 | Pro | Leu | Phe | Met | Gly 300 | Lys | Val | Val | Asn | Pro 305 | Thr | Gln | Lys |

POLYPEPTIDES AND DNA CODING THEREFOR

This invention relates to polypeptides, especially polypeptides having activity of the serine-protease inhibitor type, to DNA encoding therefor and to pharmaceutical preparations containing the inhibitor.

Proteolytic enzymes released during the inflammatory process, by neutrophils in particular, are thought to play a central role in tissue damage associated with chronic lung diseases such as pulmonary emphysema and bronchiectasis (Janoff A (1985) *Am Rev Resp Dis* 132, 417). Most individuals remain relatively healthy with minimal tissue damage following an inflammatory response because the blood and lung tissues contain several inhibitors to counteract the effects of proteinases (Stockley R (1983) *Clin Sci* 64, 119).

$\alpha_1$-antitrypsin (AAT) is a major inhibitor of serine proteinases present in the blood and in lung secretions. Its major physiological function is to protect the lower respiratory tract from neutrophil elastase, an enzyme implicated in the damage of lung connective tissue that occurs in chronic lung disease (Carell RW, Jeppsson JO, Laurell CB et al. (1982) *Nature* 298, 329).

Individuals with inherited deficiency of AAT are predisposed to developing early onset adult pulmonary emphysema particularly if they smoke (Laurell CB, Eriksson S. (1963) *Scand J Clin Lab Invest* 15, 132). Although other serine proteinase-inhibitors probably also play a role in protecting the lung from proteolytic degradation, these have either been poorly characterised or genetic abnormalities of these inhibitors have yet to be described in association with chronic lung disease. It seems likely that other genetic factors contribute to chronic lung disease. Of potential relevance are abnormalities in related proteins. Previous reports suggested that there may be immunologically cross-reacting material detected by antibodies to $\alpha_1$-antitrypsin (Glew RH, Zidian JL, Chiao JP et al (1981) In: "Electrophoresis" Walter de Gruyter, page 5115; Mittman C, Teevee B, Lieberman J (1973) *J Occ Med* 15, 33) and three related genes have been detected in a rat liver cDNA library (Krauter KS, Citron BA, Hsu MT (1986) *DNA* 5, 29) suggesting that other putative serine proteinase-inhibitors remain to be characterised.

Less than 5% of all patients who develop pulmonary emphysema have a clearly identifiable abnormality of AAT protein (Mittman C, Teevee B, Lieberman J (1973) *J Occ Med* 5, 33) and only about 10–20% of cigarette smokers are particularly vulnerable to the onset of pulmonary emphysema (Niewhoner DE (1983) In: "Textbook of Pulmonary Diseases" page 915). A polymorphism of the AAT gene that occurs in about 20% of patients with pulmonary emphysema has recently been described (Kalsheker NA, Hodgson IJ, Watkins GL et al. (1986) *Am Rev Resp Dis* 133, A219). This polymorphism may be linked to other candidate genes involved in the pathogenesis of chronic lung disease. It is now known that in humans two other potentially important genes occur within 100 kilobase pairs (kb) to AAT on chromosome 14. These are $\alpha_1$-antichymotrypsin (ACT) (Rabin M, Watson M, Kidd Vet al. (1986) *Somat Cel Mol Genet* 12, 209) and an AAT gene-related sequence (ASRG) (Lai E, Kao F, Law Met al. (1983) *Am J Hum Genet* 35, 385) which may code for a serine proteinase-inhibitor with an anti-elastase activity (according to Professor S. Woo, Baylor Medical School, Houston, Tex.).

The isolation of several AAT cDNA clones from a human liver cDNA library has previously been reported (Kalsheker N, Chiswell D, Markham A et al (1985) *Ann Clin Biochem* 2225).

Although an understanding of the structure and role of AAT is clearly of major significance in the diagnosis and potential management of pulmonary emphysema, it is clear that AAT is unlikely to provide a complete answer. A problem facing workers in the field is to identify further serine protease inhibitors, not least so that they can be studied to develop further understanding of disease such as pulmonary emphysema.

Nucleic acid having significant nucleotide sequence differences from DNA coding for AAT and ACT has now been isolated and cloned. Protein corresponding to the sequence has been made by the use of a suitable host/vector system and has displayed serine protease inhibitory activity. A new human serine protease inhibitor has therefore been discovered and prepared.

According to a first aspect of the invention, there is provided a human serine protease inhibitor whose unglycosylated molecular weight is 32 kDa±1 kDa. The molecular weight may be measured (for example by polyacrylamide gel electrophoresis (PAGE)) under conditions in which one or more of the following marker proteins have the molecular weights shown:

| | |
|---|---|
| $\alpha$-lactalbumin | 14.4 kDa |
| soybean trypsin inhibitor | 20.1 kDa |
| carbonic anhydrase | 30 kDa |
| ovalbumin | 43 kDa |
| bovine serum albumin | 67 kDa |

As will be described below, the thermal stability and pH stability characteristics of the serine protease inhibitor of this aspect of the invention may constitute additional distinctions from AAT.

The present invention provides in a second aspect a proteinaceous molecule selected from:
 (a) a molecule having the amino acid sequence shown in SEQ ID NO:1 or a sequence not differing substantially therefrom;
 b) a polypeptide having substantially the same structure and biological activity as a); and
 c) fragments, derivatives and mutants of a) or b) significantly involved in their biological activity.

The sequence from $Leu_{38}$ is identical to the terminal sequence of AAT suggesting that this sequence is significant for activity. Conversely, residues 1 to 37 serve to distinguish proteins of this invention from AAT.

Fragments of the serine protease inhibitor, other than those which are also fragments of AAT also fall within the scope of the present invention. Such polypeptides differ from AAT in having shorter sequence of different composition at the N-terminal end which it is believed from tertiary structure predictions would result in the loss of alpha-helical structure.

Accordingly the present invention provides in a third aspect a proteinaceous molecule selected from:
 (a) a polypeptide having serine protease inhibitor activity and whose amino terminus includes the sequence of amino acids 1 to 37 of SEQ ID NO: 1 or a sequence not differing substantially therefrom;
 b) a polypeptide having substantially the same structure and biological activity as a);
 c) fragments, derivatives and mutants of a) or b) significantly involved in their biological activity.

It will be understood by those skilled in the art that some variation in structure may occur in naturally occurring biologically active polypeptides but, provided that such structural variations do not eliminate biological activity of interest, for example serine protease inhibition, the present invention includes such variations within its scope. One form of variation may be to have one or more additional N-terminal amino acid residues.

It is difficult to put precise limits on the variation in amino acid residues which may be tolerated since, as will be understood by those skilled in the art, some regions and some residues are more significant than others. Conserved regions which play an important role in biological activity are likely to be less tolerant of variation and another aspect of the present invention provides polypeptides containing or consisting of one or more conserved sequences.

By "conserved" we mean having significant sequence homology with other proteins of interest. It is not possible to put precise numerical limits on the degree of homology but 25% can be significant and 80% or greater, say, would in many examples be expected to be highly significant, depending upon where the homology occurs, amongst other factors.

Derivatives of the polypeptide of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are preferably those of naturally occurring alcohols, e.g. methanol or ethanol.

Glycosylation may take place on any suitable residue; asparagine residues are particularly suitable for glycosylation, especially when they are in exposed sites on the tertiary structure. Glycosylation at sites corresponding to the natural sites of glycosylation of AAT may be preferred, at least in the common portion of the sequence. It appears that glycosylation is not essential for biological activity.

Further derivatives are salts, especially pharmaceutically acceptable salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine and the like.

Mutants of the polypeptides of the invention are characterised in the exchange of one (point mutant) or more, about up to 10, of its amino acids against one or more of another amino acid. They are the consequence of the corresponding mutations at the DNA level leading to different codons. Natural and synthetic mutants are included within the scope of the invention.

Further variations which may be acceptable include for example, fusion proteins, conservative mutants, allelic variation, polymorphisms, oligomeric forms and the like, provided these do not affect essential features of composition, structure or activity to an unacceptable degree.

Proteinaceous molecules in accordance with the invention may be prepared or, if natural, isolated by any suitable means. Synthesis will generally be preferred even for natural molecules, although semi-synthetic preparations may be more appropriate under some circumstances. According to a further aspect of the invention, there is provided a process for the preparation of a proteinaceous molecule as described above, the process comprising coupling together successive amino acid residues and/or ligating oligo- and/or polypeptides. Glycosylation or other modification may take place at any suitable stage, if desired.

Although proteinaceous molecules in accordance with the invention of the present invention may be prepared by chemical synthesis, where the number of amino acid residues is not too large, it is preferred to prepare them by translation of RNA. While in vitro RNA translation systems may be appropriate under some circumstances, DNA expression will generally be the method of choice.

According to a further aspect of the invention, there is therefore provided recombinant or isolated DNA encoding a proteinaceous molecule as described above.

Preferred DNA in accordance with the invention codes for the amino acid sequence shown in SEQ ID NO:1 or for a polypeptide having serine protease inhibitor activity and whose amino terminus includes the sequence of amino acids 1 to 37 of SEQ ID NO: 1 or a sequence not differing substantially therefrom. It will be appreciated that although the nucleotide sequence shown in SEQ ID NO:1 may itself be preferred for expression, the degeneracy of the genetic code means that many nucleotide sequences can code for a given amino acid sequence. DNA in accordance with the invention may consist essentially of DNA as described above or may additionally include other sequences.

Fragments, derivatives and mutants of proteinaceous molecules of the invention may be encoded by DNA which is similar to DNA encoding at least part of the amino acid sequence shown in SEQ ID NO:1. Similarity may be gauged by hybridisation experiments. DNA which hybridises, for example under stringent conditions, to at least part of the DNA sequence shown in SEQ ID NO:1, or to another DNA sequence encoding at least part of the amino acid sequence shown in SEQ ID NO:1 forms part of the invention. Stringent conditions are exemplified by 35°–65° C. at a salt concentration of about 0.9 molar.

Recombinant DNA in accordance with the invention may be in the form of a vector. The vector may for example be a plasmid, cosmid or phage or other virus. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present. Vectors not including regulatory sequences are useful as cloning vectors. Suitable vectors include the plasmid pKK 233-serpin.

Cloning vectors can be introduced into *E. coli* or another suitable host which facilitate their manipulation. Suitable hosts include a K12 strain of *E. coli* JM105. As glycosylation does not appear to be essential for biological activity, expression may take place in prokaryotes or eukaryotes. *E. coli* will usually be the prokaryotic organism of choice. As for eukaryotes, although yeasts such as *Saccharomyces cerevisiae* may be suitable, the different glycosylation patterns of yeasts may mean that other eukaryotic expression hosts are preferred. Insect cells, such as those transfected with Baculovirus, may be used as may mammalian cells such as COS cells, which could for example be SV40-transfected. According to another aspect of the invention, there is therefore provided a host cell transfected or transformed with DNA as described above.

DNA in accordance with the invention can be prepared by any convenient method involving coupling together successive nucleotides, and/or ligating oligo- and/or poly-nucleotides, including in vitro processes, but recombinant DNA technology forms the method of choice.

DNA of the present invention may be recovered from cDNA libraries by methods known in the art and it will be understood that, once the nucleotide sequence is known, direct amplification is possible by the polymerase chain reaction, for example. (Saiki et al, *Science* (1985) 230 1350-1354). Recombinant DNA sequences in accordance with the invention can be prepared entirely from using publicly and commercially available materials. For example, a human liver cDNA library can be used, such as the Derek Woods Library (Children's Hospital, 300 Longwood Ave, Boston, *Mass.* 02115, U.S.A.). Alternatively, cDNA can be prepared from total human RNA using reverse transcriptase.

CG tails can be added to cDNA by the homopolymeric tailing techniques The resulting tailed cDNA can be screened with an $\alpha_1$-antitrypsin probe (which may be synthetic or a fragment of or the whole natural sequence), which enables identification of putative positive clones. A PstI fragment can then be isolated, by virtue of the CG tailing.

The DNA of the present invention may also be useful for diagnostic, screening, or other purposes.

From the cDNA sequence of SEQ ID NO:1, it has been established that there are regions of unique DNA sequence corresponding to regions of unique amino acid sequence. The sequence of 5 amino acid residues is considered sufficient to confer a greater than 90% probability of uniqueness for a protein. One or more short unique stretches may be used to synthesise chemically unique peptides—this service is available commercially—to raise specific antibodies. Specific polyclonal antibodies may be tested for reactivity to human serum and to liver homogenate to investigate if the protein is present in both tissues using antibodies that do not react with AAT or ACT.

Proteinaceous molecules of the present invention may be useful for example, in the treatment of conditions associated with deficiency of serine protease inhibitors. They may thus display leukocyte elastase inhibitor, cathepsin G inhibitor, trypsin inhibitor and/or pancreatic elastase inhibitor activities, suggesting utility in the treatment of such conditions as emphysema, arthritis or septic shock.

In a further aspect, the invention therefore provides a proteinaceous molecule as described above for use in medicine.

The invention also provides the use of a proteinaceous compound as described above in the manufacture of a medicament for the treatment or prophylaxis of emphysema, arthritis or septic shock. The invention also provides a method for the treatment or prophylaxis of emphysema, arthritis or septic shock, the method comprising administering to a patient an effective, generally non-toxic, amount of a proteinaceous compound as described above.

The invention further provides pharmaceutical preparations containing as an active ingredient one or more proteinaceous compounds as described above. Such preparations may be formulated with suitably acceptable carriers for administration as inhalants or parenterally, for example. Preparations adapted for parenteral administration will usually be sterile.

Heat stability tests indicate that the polypeptides of the present invention may be more stable to heat treatment (for example at 60° C. for 30 minutes) than human serum and/or than AAT; however, the pH stability appears to be less than that of AAT (for example at pH <4.5 proteins of the invention may at least in some circumstances be inactivated, whereas some (such as about 30%) activity may be retained by AAT, and at pH >9 proteins of the invention may be inactivated.

The present invention also provides antibodies to the proteinaceous molecules of the invention. They may be made by techniques known in the art (see for example: "Antibodies, A Laboratory Manual", E. Harlow and D. Lane, Cold Spring Harbor, 1988) and may include polyclonal and monoclonal antibodies which may be useful inter alia for diagnostic purposes, e.g. in diagnosis of deficiency states. Should abnormalities associated with predisposition to disease be identified, such information could provide a potential risk assessment.

Specific embodiments of the invention will now be described by way of example only and with reference to the sequences shown in SEQ ID NO:1, which shows the sequence of amino acid residues for a preferred polypeptide of the present invention and DNA sequence (as a BamHI/HindIII fragment) encoding it.

EXAMPLE 1

Isolation and Sequencing

A cDNA library was prepared from human liver poly A+ messenger RNA and cloned into the PvuII site of the plasmid vector pAT153 which had BamHI and HindIII linkers attached. The library consisted of 100,000 individual recombinants. Five thousand independent colonies were screened using a radioactively labelled 1350 base pair (bp) DNA probe corresponding to the coding sequence of the AAT gene. After repeated screening a clone was isolated which contained restriction fragments that were different to what was expected. It contained an unusually large BamHI/ HindIII fragment on digestion with both restriction enzymes. The predicted size of the BamHI/HindIII, for AAT, should have been about 130 bp but the actual fragment was found to be about 350 bp. A sample of the cloned cell-line, under the description *E. coli* K12 strain, HB101-clone A5 (plasmid pAT153), was deposited at the NCIMB, Torrey Research Station, PO Box 31, 135 Abbey Road, Aberdeen, United Kingdom, AB9 8DG on 15th December, 1989 with Accession Number 40237.

The BamHI/HindIII fragment was cloned into M13 (mp18 and mp19) for sequencing and contained sequence which was different from that for AAT. The sequence corresponded to untranslated regions at the 3'end of the cDNA clone.

The DNA sequence of SEQ ID NO:1 also contains two intermediate BamHI restriction site at nucleotide positions 1 to 6 and 991 to 996. The 1000b BamHI/BamHI fragment was sequenced and this also contained significantly different sequence at the 5' end. Using the nomenclature of Long et al., *Biochemistry* 1984, 23, 4828, for AAT, the bases from 126 to 15 were inverted, 127–486 were missing and the remainder of the sequence was identical to AAT including the active site.

The nucleotide and corresponding amino acid residue sequences are represented in SEQ ID NO:1; the coding region runs from nucleotide residue 3 (a first isoleucine) to 929 (a stop codon). It will be noted that the BamHI sites are at positions 1 to 6 and 991 to 996, respectively.

EXAMPLE 2

Expression of pKK233-2

A BamHI fragment, containing the first exon of AAT in reverse orientation, and sequence from base 487 to 1380 (using the numbering system of Long et al.) in the same orientation as AAT was cloned into the plasmid expression vector pKK233-2 in a reading frame that would correspond to AAT. The cloning was achieved by filling in the ends of BamHI fragment, ligating an 8 base linker (GCCATGGC) containing a recognition site for the restriction enzyme NcoI (CCATGG), cutting with NcoI and cloning the fragment into the NcoI site of the vector pKK233-2 This fragment if in the correct orientation would result in the expression of an unfused protein in E. coli in the same orientation as AAT.

A K12 strain of E. coli, JM105, was used as a host cell and a sample of the transformed cell line, under the description E. coli, K12 strain JM105-clone pKK233-serp (plasmid pKK-2), was deposited at the NCIMB, Torrey Research Station, PO Box 31, 135 Abbey Road, Aberdeen, United Kingdom, AB9 8DG, on 21st Dec., 1989 with Accession Number 40244.

Transformed cells were expressed by growing them up to an optical density of 0.3 and then adding 10 mM IPTG (isopropylthiogalactoside), an inducer of the β-galactosidase gene, which is placed in front of the cloned gene fragment and growing cells for 5 hr at 37° C.

The foreign protein expressed had a molecular weight of 32 kDa±1 kDa on PAGE under conditions in which one or more of the following marker proteins have the molecular weights shown:

| α-lactalbumin | 14.4 kDa |
| soybean trypsin inhibitor | 20.1 kDa |
| carbonic anhydrase | 30 kDa |
| ovalbumin | 43 kDa |
| bovine serum albumin | 67 kDa. |

EXAMPLE 3

Expression of pNH18a

The BamHI fragment extending from nucleotide position 1 to 996 (Example 1) was cloned into the BamHI site of the expression vector pNH18a. A sample of the cloned cell line, under the description E. coli K12 strain D1210HP (plasmid pNH18a) was deposited at the NCIMB, Torrey Research Station, PO Box 31, 135 Abbey Road, Aberdeen AB9 8DG, United Kingdom on 5th Dec. 1990 under Accession No. NCIMB 40341. pNH is a vector that contains two invertible promoters in tandem. Expression of inserts is regulated by heat-induced inversion of the prokaryotic promoters. Inversion is accomplished by site-specific recombination which is mediated by the phage Int product of the E. coli host strain D1210 HP and attB and attP recognition sequences of the plasmid. A heat-pulse switches the promoter from the "OFF" to the "ON" position and the Int-mediated conversion is 95% efficient.

The details of induction and expression are as follows. Bacterial (D1210HP) were grown to an optical density of 0.3 (measured at 600 nm) in 250 ml of LB-broth. The cells were heat-pulsed at 42° C. for 2 minutes and IPTG was added to a final concentration of 1 mM. The cells were grown overnight at 37° C. and then centrifuged at 500 g for 15 minutes at 4° C. The cells were resuspended in 3 ml of lysis buffer (50 mM Tris-HCl-pH 8.0, 1 mM EDTA, 100 mM NaCl)/g of cells. Phenylmethylsulphonylfluoride (PMSF) (8 μl/g), lysozyme (10 mg/ml) and deoxycholic acid (4 mg/g) were added. The mixture was placed in a 37° C. waterbath, stirred and then incubated with 20 μl of DNAaseI (1 mg/ml)/g of cells till the mixture was no longer viscous. The cell lysate was centrifuged at 12000 g for 15 minutes at 4° C. The pellet was resuspended in 0.1 mM PMSF and 8M urea and left for 1 hour at room temperature. This solution was treated with 9 volumes of 50mM $KH_2PO_4$ (pH 10.7), 1 mM EDTA (pH 8.0) and 50 mM NaCl for 30 minutes the pH was then adjusted to 8.0 with HCl. The mixture was centrifuged at 12000g for 15 minutes at room temperature and the pellet was resuspended for further analysis.

EXAMPLE 4

Activity of protein expressed from pKK233-2

Cells from Example 2 were pelleted, washed in physiological saline and after two cycles of osmotic lysis followed by freeze/thawing the supernatants were analysed for biological and immunological activity. From a 5ml culture approximately 400 μl of supernatant was collected and by immunochemical measurements with antibodies to human alpha-antitrypsin approximately 1.4 μg of protein was obtained. Using an assay for the inhibition of elastase 15 μl of this preparation (approximately 50 ng) had an activity equivalent to about 0.1 ml of human serum. This activity is nearly identical when related to the amount of protein. Studies of heat stability demonstrated that the expressed protein was stable to heat treatment (65° C. for 20 minutes) whereas human serum under similar treatment showed loss of activity.

EXAMPLE 5

Activity of protein expressed from pNH18a

The expressed protein from pNH18a (Example 3—N-CIMB 40341) was examined for stability by exposure to heat and to pH changes. Activity was measured as described in Example 4 above. When heated to 60° C. for 30 minutes the protein retained functional activity when compared with alpha-1-antitrypsin (AAT). The activity was about 30% of untreated sample whereas with AAT there was virtually no activity detectable suggesting that the expressed protein was relatively more thermostable. On exposure to acid pH, the expressed protein was inactivated by pH<4.5 whereas AAT retained approximately 30% of its activity. At pH>9.0 the expressed protein was inactivated. One point of note is the presence of glycosylated residues in AAT which may influence the stability and are not present in the expressed protein.

I claim:

1. A protein having the amino sequence shown in SEQ ID NO: 2.
2. The protein of claim 1 which is glycosylated.

* * * * *

UNITED STATES PATENT AND TRADEMARK OFFICE
CERTIFICATE OF CORRECTION

PATENT NO. : 5,412,073
DATED : May 2, 1995
INVENTOR(S) : Ahmed N. Kalsheker

It is certified that error appears in the above-identified patent and that said Letters Patent is hereby corrected as shown below:

On the Title page, item [75] Inventor should read --Noor Ahmed Kalsheker--.

Signed and Sealed this

Ninth Day of July, 1996

Attest:

BRUCE LEHMAN

Attesting Officer

Commissioner of Patents and Trademarks